United States Patent
Rogozinski (10) Patent No.: US 6,565,568 B1
(45) Date of Patent: May 20, 2003

(54) APPARATUS AND METHOD FOR THE MANIPULATION OF THE SPINE AND SACRUM IN THE TREATMENT OF SPONDYLOLISTHESIS

(76) Inventor: Chaim Rogozinski, 3223 Front Rd., Jacksonville, FL (US) 32217

( * ) Notice: Subject to any disclaimer, the term of this patent is extended or adjusted under 35 U.S.C. 154(b) by 271 days.

(21) Appl. No.: 09/672,680

(22) Filed: Sep. 28, 2000

(51) Int. Cl.[7] .............................................. A61B 17/56
(52) U.S. Cl. ........................... 606/61; 606/73; 606/102; 606/105
(58) Field of Search ........................... 606/57, 61, 105, 606/53, 90, 162, 205, 206

(56) References Cited

U.S. PATENT DOCUMENTS

| | | |
|---|---|---|
| 2,002,021 A | 5/1935 | Rouse |
| 2,774,350 A | 12/1956 | Cleveland, Jr. |
| 3,709,219 A | 1/1973 | Halloran |
| 3,960,147 A | 6/1976 | Murray |
| 4,102,339 A | 7/1978 | Weber et al. |
| 4,361,144 A | 11/1982 | Slatis et al. |
| 4,854,304 A | 8/1989 | Zielke |
| 4,898,161 A | 2/1990 | Grundei |
| 4,988,349 A | 1/1991 | Pennig |
| 5,219,349 A | 6/1993 | Krag et al. |
| 5,385,565 A * | 1/1995 | Ray ............................ 606/61 |
| 5,490,851 A | 2/1996 | Nenov et al. |
| 5,662,648 A | 9/1997 | Faccioli et al. |
| 5,672,175 A | 9/1997 | Martin |
| 5,704,937 A | 1/1998 | Martin |
| 5,899,901 A | 5/1999 | Middleton |
| 5,984,922 A * | 11/1999 | McKay ........................ 606/61 |
| 6,017,343 A | 1/2000 | Rogozinski |
| 6,090,113 A * | 7/2000 | Le Couedic et al. .......... 606/61 |

* cited by examiner

Primary Examiner—Todd E. Manahan
(74) Attorney, Agent, or Firm—Thomas C. Saitta (57) ABSTRACT

An apparatus and a method for performing spondylolisthesis reduction utilizing spinal link implants, the apparatus comprising a jack which is temporarily affixed to the spinal links, where the jack is constructed to provide leverage or fulcrum points such that the vertebrae or sacrum can be moved as required for, proper realignment and to position adjacent link members for connection. The jack comprises a pair of outrigger members connected to a levering member such that each is free to pivot, whereby the relative angle between the members may be altered by movement of the levering member, which is provided with at least one handle to be gripped by the surgeon. Optionally, an outrigger stabilizer member is also provided. The ends of the outrigger members are provided with connector means for temporarily securing the outriggers to the linking members in a secure manner such that any manipulation of the outrigger members is transferred to the spinal link members and thus to the vertebra or sacrum to which they are affixed. With the sacrum and vertebrae properly aligned and positioned, the spinal links are joined to form a rigid structure and the jack is removed.

41 Claims, 6 Drawing Sheets

APPARATUS AND METHOD FOR THE MANIPULATION OF THE SPINE AND SACRUM IN THE TREATMENT OF SPONDYLOLISTHESIS

BACKGROUND OF THE INVENTION

This invention relates generally to the field of medical devices and methods of treatment of spondylolisthesis, and more particularly to the field of such devices and methods for manipulation of adjacent vertebrae or of the lower vertebrae and the sacrum (which in humans is formed of fused vertebrae), whereby the adjacent vertebrae or the vertebrae and sacrum are properly aligned and positioned such that fixation structures can be utilized to secure the adjacent vertebrae or the vertebrae and sacrum in the proper relation. Even more particularly, the invention relates to a mechanical apparatus or jack which can be temporarily attached to spinal implants permanently affixed to both the vertebrae and the sacrum, whereby the surgeon performs the spondylolisthesis reduction by manipulating the jack to properly position the vertebrae and sacrum and then securing the sacrum spinal implant to the vertebral, spinal implant in rigid manner.

The invention herein functions with and incorporates portions of the apparatus and method disclosed in my U.S. Pat. No. 6,017,343, issued Jan. 25, 2000, and entitled Apparatus, Method and System for the Treatment of Spinal Conditions and Fixation of Pelvis and Long Bones, the disclosure of which is herein incorporated by reference. The invention will also function with other types of spinal implants and mechanical fixation devices used to create a construct which will secure the adjacent pairs of vertebrae or the sacrum and vertebrae in a fixed, rigid relationship, such as plates or rods.

The lumbar vertebrae comprise the five vertebrae positioned below the dorsal vertebrae, and are customarily designated L1 through L5, with L1 being adjacent the lowermost or twelfth dorsal vertebra and L5 being adjacent the sacrum. The sacrum is a large, curved, triangular bone having a wide base which articulates from the L5 vertebra. The anterior surface of the sacrum is generally concave, curving in a pronounced manner from above downward and slightly from side to side. Spondylolisthesis is a condition where adjacent vertebrae, most usually the sacrum and the lower or lumbar vertebrae, are not properly aligned or connected, such that adjacent vertebrae are displaced or the lumbar vertebrae are displaced anteriorly from the upper base of the sacrum. For purposes of this disclosure, the apparatus and method shall be described primarily with reference to spondylolisthesis occurring between the L5 vertebra and the sacrum, but it is to be expressly understood that the apparatus and method are suitable for manipulation and treatment of any adjacent vertebrae. In a spondylolisthesis reduction, the surgeon properly repositions the vertebrae and sacrum, and then permanently joins the vertebrae and sacrum using mechanical fixation structures. The reduction may require manipulation of the vertebrae and the sacrum in one or more directions, i.e., translation in the anterior/ventral or posterior/dorsal direction, compression or distraction in the longitudinal direction of the vertebral axis, and rotation about the vertebral axis, as well as pivotal flexion of the sacrum in the ventral direction or pivotal extension of the sacrum in the dorsal direction.

In my U.S. Pat. No. 6,017,343, spinal implants comprising linking members are disclosed which comprise a central portion joining two end portions, the end portions being apertured to receive a pedicle bolt whereby the link members can be permanently affixed to a vertebra or other bone. The end portions of adjacent link members are aligned to receive a single pedicle bolt and a lock nut, and in this manner pairs of link members can be connected to form a rigid linking structure, where the link members can be affixed to adjacent vertebrae, bones or bone segments in order to create a rigid connecting structure which secures the vertebrae, bones or segments in fixed manner.

It is an object of this invention to provide an apparatus, a system and a methodology for the manipulation and fixation of adjacent vertebrae or the lumbar vertebrae and the sacrum for spondylolisthesis reduction, whereby a mechanical manipulator device or jack is provided which allows the surgeon to properly position and secure the vertebrae and sacrum in a relatively quick and straightforward manner. It is a further object to provide such an apparatus and method which enables the surgeon to translate, compress, distract, rotate, flex or extend either or both the vertebrae and the sacrum as required, which is easily connected to and removed from spinal implant link members affixed to the vertebrae and the sacrum, and which functions to retain proper positioning of the vertebrae and sacrum as the surgeon connects the link members of the sacrum to the link members of the vertebrae. It is a further object to provide such an apparatus whose component parts are adjustable to accommodate variation in patient size and to present a variety of angular combinations as required for a particular reduction operation. These and other objects not expressly stated above will be readily apparent from examination of the disclosure to follow.

SUMMARY OF THE INVENTION

The invention comprises an apparatus and a method for performing spondylolisthesis reduction between adjacent vertebrae and more particularly between the lower vertebrae and the sacrum, where the method utilizes spinal implants, such as spinal link members comprising central portions bridging two apertured end portions, where the end portions of two such link members may be aligned to receive a pedicle bolt, a bolt which is driven into the vertebral body or the sacrum, or a joining bolt which is independent of the vertebral body or sacrum, such that the two link members can be secured to the vertebra or sacrum and to each other by lock nuts to form a rigid structure. The apparatus comprises a jack or manipulator device which is temporarily affixed to transversely mounted central portions of the spinal links, where the jack is constructed to provide leverage or fulcrum points such that the vertebrae or sacrum can be moved as required for proper realignment and to position adjacent link members for connection. The jack apparatus comprises a pair of outrigger members connected to a levering member, where the outrigger members and levering member are provided with plural apertures to receive pivot bolts, in order to allow for variation in the relative angular and linear dispositions of the members. The outrigger members and levering member are connected such that each is free to pivot, whereby the relative angle between the members may be altered by movement of the levering member, which is provided with at least one handle to be gripped by the surgeon. Optionally, an outrigger stabilizer member is also provided for attachment to the outrigger members in similar manner, such that the combination of the outrigger members, levering member and stabilizer member defines a four-sided polygon. The ends of the outrigger members are provided with connector means for temporarily securing the outriggers to the transverse portions of the linking members in a secure manner such that any manipulation of the outrigger members is transferred to the spinal link members and thus to the vertebra or sacrum to which they are affixed. The connector means preferably comprises a hook member which receives the transverse portion of the linking member and a threaded locking ring which can be translated against the transverse portion to secure it against the hook member of the outrigger member. The apparatus is also preferably provided with a position locking member which comprises an elongated body pivotally attached to the levering member, where the position locking member can be temporarily secured to one of the outrigger members to prevent relative movement between the outrigger members and the levering member in order to secure the apparatus in a particular angular configuration.

The preferred method comprises the steps of affixing spinal linking members to dorsal side of the base of the sacrum and to the dorsal side of at least the L5 vertebrae, or to any adjacent vertebrae. The spinal link members affixed to the sacrum preferably comprise one transversely mounted linking member whose central portion defines a transverse bridging member extending laterally across the sacrum and two longitudinally disposed linking members, where one end of each longitudinally disposed linking member is secured to an end of the transversely mounted linking member while the other end of each longitudinally disposed linking member remains free. A pair of longitudinally disposed linking members are each affixed to the L4 and L5 vertebra (an L4 to L5 fusion being representative of this technique), or to any two adjacent vertebrae that are slipped relative to each other, and a transversely mounted linking member is affixed across the L4 vertebra and connected to the longitudinally disposed linking members. Another pair of longitudinally disposed linking members are connected to the longitudinally disposed linking members on the L5 vertebra, with each having a free end. After proper reduction has been achieved, the free ends of the longitudinally disposed linking members on the sacrum and the L5 vertebra will be connected using a bolt and lock nut. To manipulate the vertebrae and sacrum as required, the outrigger members are joined to the transverse members of the spinal link members on the L4 vertebra and the sacrum, such that the outrigger members extend in the dorsal direction. The outrigger stabilizer member and levering member are then connected to the outrigger members to define a polygonal configuration, which may be a parallelogram, a trapezoid or other four-sided configurations. The surgeon then manipulates the vertebrae and sacrum as required by pulling on the levering handle and secures the apparatus against angular movement once proper positioning is achieved and the free ends of the longitudinally disposed linking members are aligned. The relative positions of the outrigger members and the levering member and stabilizer member may be changed during the course of the reduction as required to provide proper leveraging and positioning. The free ends of the linking members are then connected to form a rigid, interlocked construct which extends from the L4 vertebra through the L5 vertebra to the sacrum. The jack apparatus is then removed from the spinal link members.

DETAILED DESCRIPTION OF THE INVENTION

Figure 1:
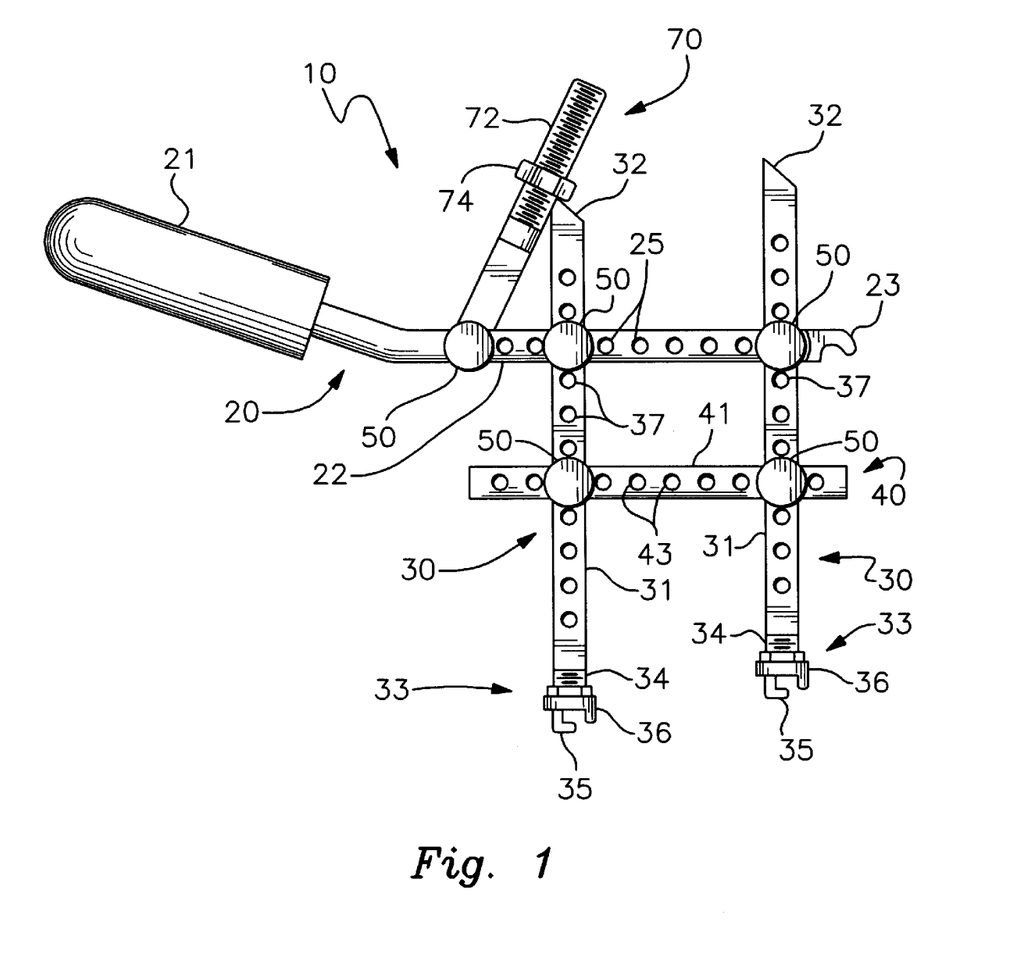
FIG. 1 is a side view of the invention, showing the relationship between the levering member, outrigger members, stabilizer member and position locking member.
Figure 10:
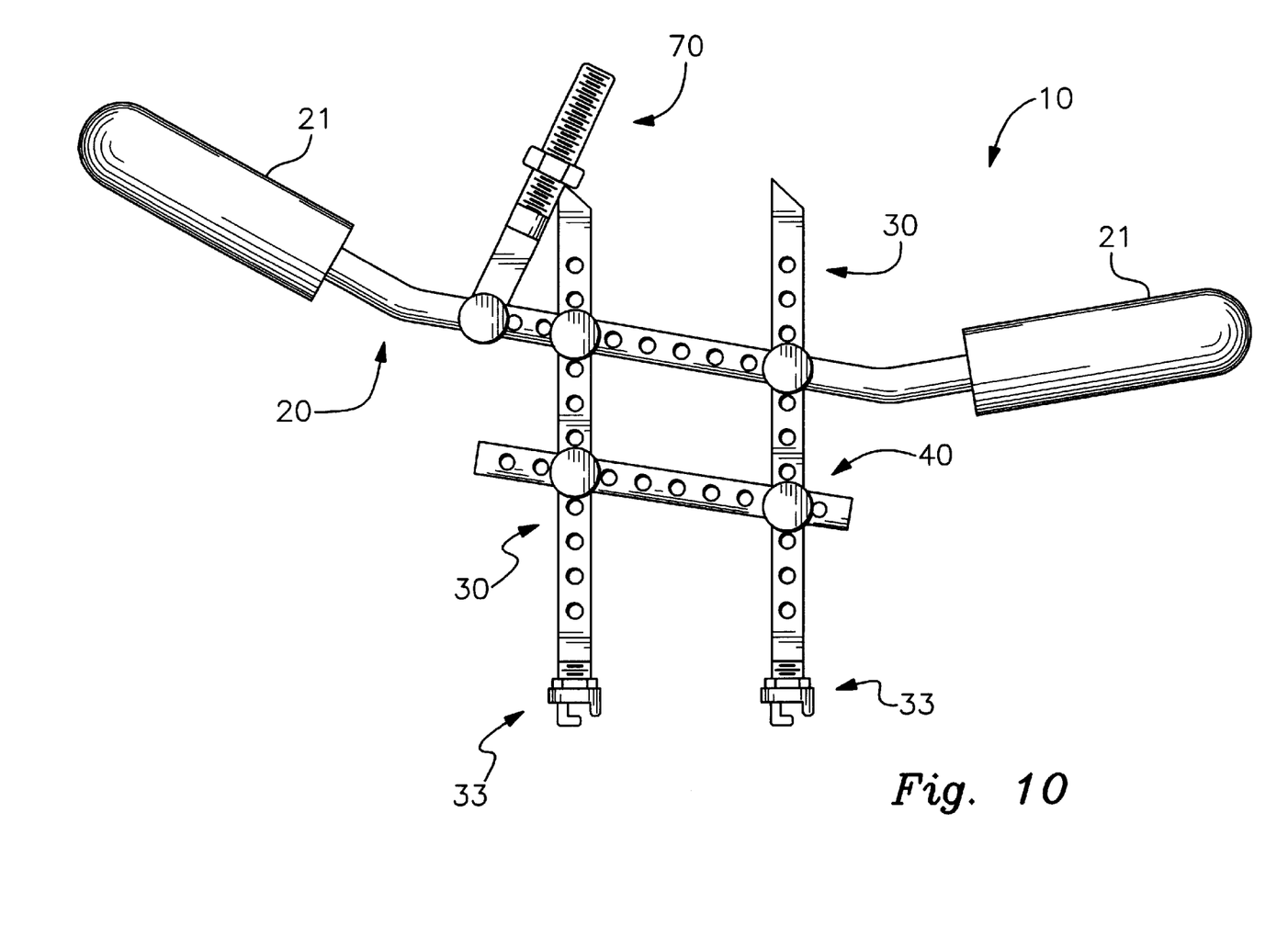
FIG. 10 is a side view of an alternative embodiment of the invention showing two handles, where the angular relation between the outrigger members and the levering member and stabilizing member have been altered during the reduction process.

With reference to the drawings, the invention will now be described in detail with regard for the best mode and the preferred embodiment, inclusive as to the apparatus, the system utilizing the apparatus and the spondylolisthesis reduction method and method of use of the apparatus. As shown comprehensively in FIGS. 1 and 10, and with individual components illustrated in FIGS. 2 through 9, the apparatus aspect of the invention is in general a manipulator or jack apparatus 10 comprising a levering member 20, a pair of outrigger members 30, and possibly a stabilizer member 40 and a positioning locking member 70. The outrigger members 30 are connected to the levering member 10 and the stabilizer member 40 in a manner which allows these components to pivot or move angularly relative to each other within a plane containing these components. In general, the combination of the levering member 20, outrigger members 30 and stabilizer member 40 defines a four-sided polygonal interior space. The combination may define a parallelogram, as shown in FIGS. 1 and 10 where the levering member 20 remains parallel to the stabilizer member 40 and where the outrigger members 30 remain parallel to each other as the angles between the components are changed, or the combination may define any four-sided polygonal shape where one or both sets of opposing components are not connected so as to be in parallel. In this discussion, taking the spine as the starting point, the term dorsal shall be taken to refer to the direction to the rear of the spine during the reduction procedure, i.e., outwardly through the patient's back, the terms ventral or anterior shall be taken to refer to the direction to the front of the spine, the term proximal shall refer to the axial direction to the top of the spine and the term distal to the axial direction to the bottom of the spine. The term longitudinal shall refer to the direction along the spinal axis and the term transverse shall refer to the direction generally perpendicular to the spinal axis and perpendicular to the dorsal and ventral directions. The apparatus and method shall be more particularly described and illustrated herein with regard to spondylolisthesis occurring between the L5 vertebra and the sacrum, but it is to be understood that the apparatus and method are equally applicable to spondylolisthesis occurring between any adjacent vertebrae.

Figure 2:
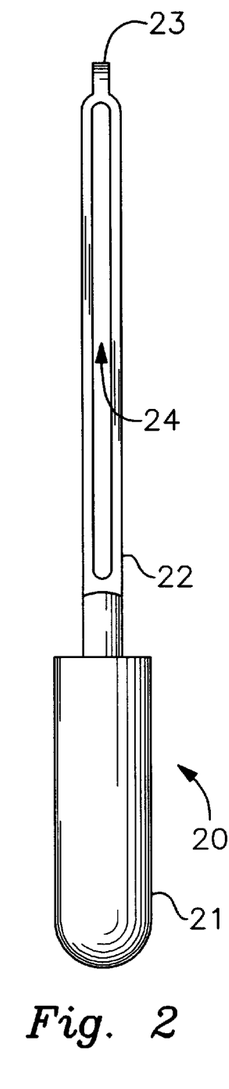
FIG. 2 is a view of the levering member taken from the dorsal direction.
Figures 8, 9:
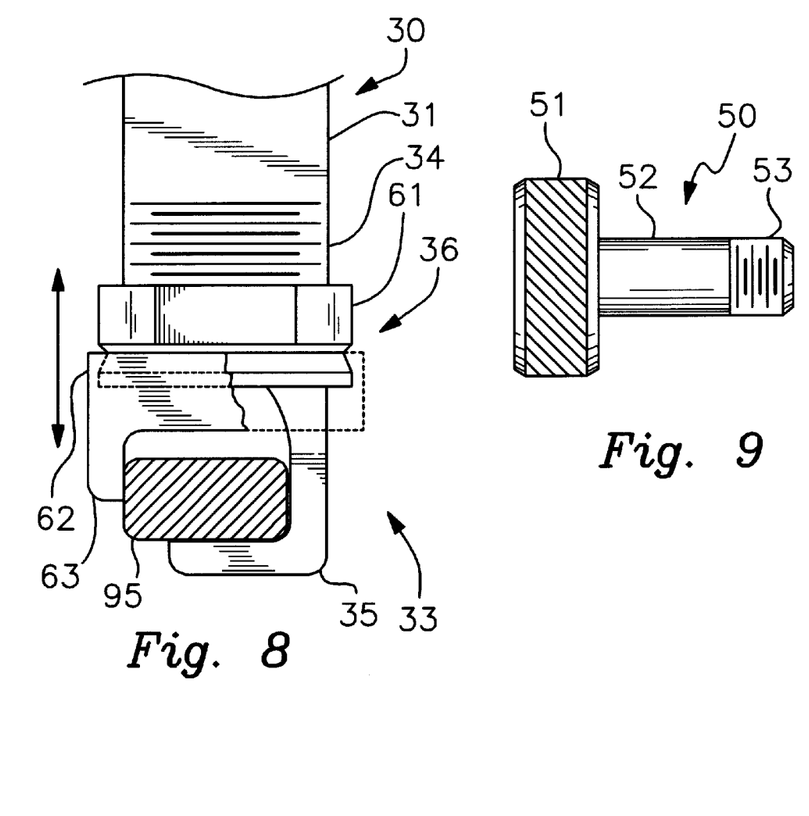
FIG. 8 is partial view of the outrigger member, showing the connector means for joining the outrigger to the transverse portion of the linking member.
FIG. 9 is a view of a pivot bolt member.
Figure 13:
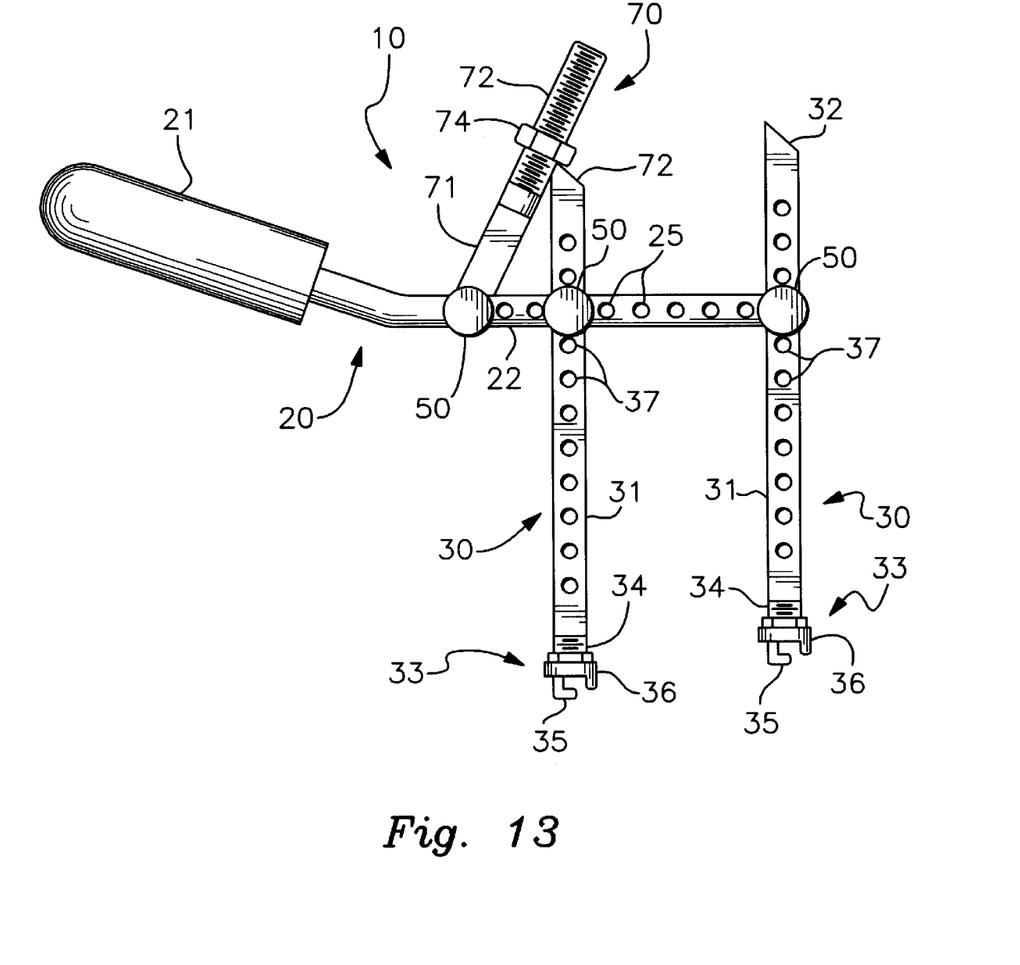
FIG. 13 is a view similar to FIG. 10, where the stabilizing member is not present.

The levering member 20 comprises an elongated main body 22 having a free distal end 23 and a proximally mounted handle 21, or as shown in FIGS. 10 and 13 both a proximally mounted handle 21 and a distally mounted handle 21 replacing free distal end 23, where the main body 22 is provided with a longitudinally extended slot 24 which passes completely through the main body 22 in the dorsal/ventral direction, as seen in FIG. 2. Preferably the handle, or handles, 21 is disposed angularly from the central axis of the main body 22 in the dorsal direction. A plural number of longitudinally spaced apertures or bores 25 for receiving the pivot bolts 50 are disposed transversely through the main body 22 and slot 24, with the apertures 25 being internally threaded on one side only to securely receive the threaded end 53 of the pivot bolts 50, which as shown in FIG. 9 comprise a large head 51, preferably knurled or scored on the radial surface for better gripping purposes, a non-threaded central body portion 52 and the threaded end 53, where the non-threaded body 52 resides within the slot 24 when the bolt 50 is inserted completely into the apertures 25. The main body 22 may be circular in cross-section as shown and the distal end 23 may have a hooked configuration as shown.

Figures 3, 4:
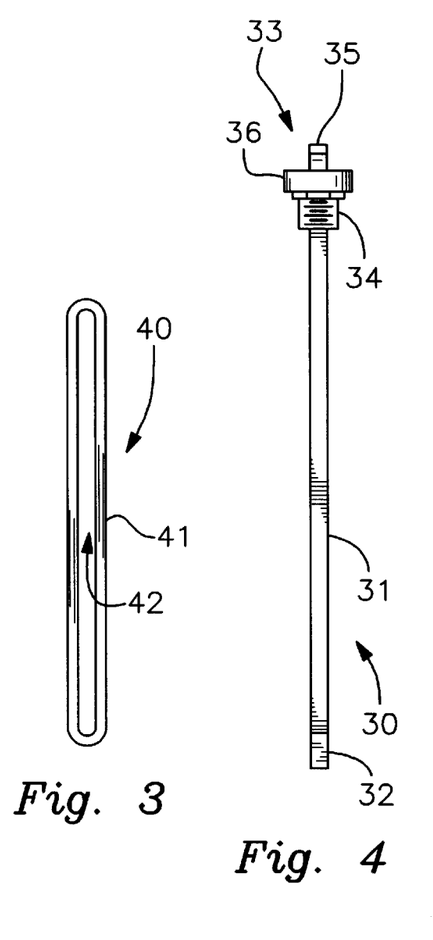
FIG. 3 is a view of the stabilizer member taken from the dorsal direction.
FIG. 4 is a view of an outrigger member taken along the vertebral axial direction.

The stabilizer member 40 comprises a main body 41 which also has a longitudinally extending slot 42 passing completely through the main body 41 in the dorsal/ventral direction, as seen in FIG. 3. A plural number of longitudinally spaced apertures or bores 43 for receiving the pivot bolts 50 are disposed transversely through the main body 41 and slot 42, with the apertures 43 being internally threaded on one side only to securely receive the threaded end 53 of the pivot bolts 50. Preferably the apertures 43 in the stabilizer member 40 and the apertures 25 in the levering member 20 are of the same number and identically spaced.

Figure 5:
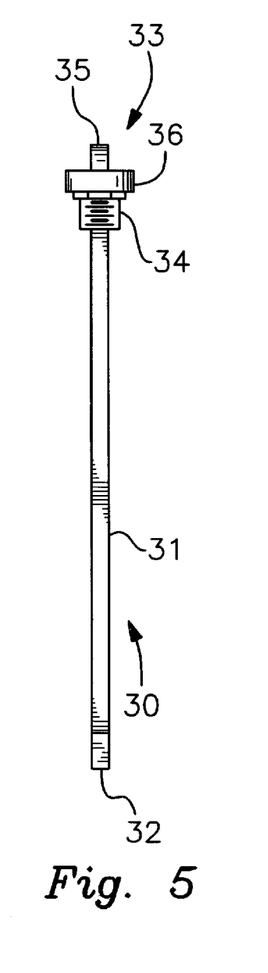
FIG. 5 is a view of the outrigger member of FIG. 4 taken along the opposite vertebral axial direction.

The outrigger members 30, shown in dorsal and proximal views in FIGS. 4 and 5, each comprises a main body 31, which is generally rectangular in cross-section, an angled dorsal end 32, and connector means 33 on the ventral end. The main body 31 is provided with transversely extending apertures 37, non-threaded, at spaced intervals. The apertures 37 receive the body portion 52 of the pivot bolts 50. The main body 31 is sized to fit within the levering member slot 24 and the stabilizer member slot 42, such that the levering member 20 and the stabilizer member 40 can be positioned at various points on the outrigger members 30 by aligning the corresponding apertures 25 or 43 with the outrigger apertures 37 and fastening a pivot bolt 50. The connector means 33 defines the mechanism for releasably securing the outrigger member 30 to the transverse bridging member 95 of the spine link members 90, and as best shown in FIG. 8 comprises in combination an externally threaded segment 34 adjacent the main body 31, a ventrally disposed hook member 35 which extends in the longitudinal direction, and a locking ring member 36 comprising an internally threaded nut 61 to mate with the externally threaded segment 34, a collar member 62 joined to the nut 61 in a manner that allows the collar 62 to rotate independently of the nut 61, and a longitudinally extending flange member 63. With the transverse bridging member 95 of the spine link member 90, which is generally rectangular in cross-section, disposed between the hook member 35 and the collar 62, rotation of the nut 61 relative to the outrigger member 30 in the proper direction causes the connector means 33 to advance to secure the transverse bridging member 95 in the rectangular space defined by the combination of the hook member 35, collar 62 and flange 63, whereby movement by the surgeon of the outrigger member 30 in any direction is transferred directly to the spine link member 90. Disconnection of the outrigger member 30 from the spine link member 90 is accomplished by reversal of these steps.

Figure 6:
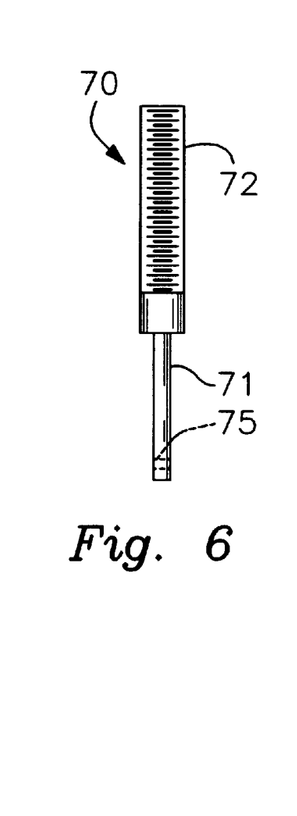
FIG. 6 is a view of the position locking member taken from the dorsal direction.
Figure 7:
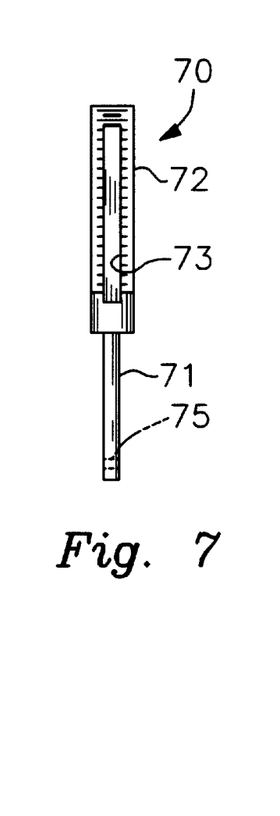
FIG. 7 is a view of the position locking member of FIG. 6 taken from the ventral direction.

The jack 10 is preferably provided with a position locking member 70, shown in the opposing longitudinal views in FIGS. 6 and 7, which allows the surgeon to lock the levering member 20, outrigger members 30 and stabilizing member 40 in a particular angular configuration relative to tension in the ventral direction. The position locking member 70 comprises an insertion body 71, generally rectangular in cross-section, an externally threaded end 72 and a non-threaded aperture 75 positioned in the insertion body 71. The insertion body is sized to fit within the levering member slot 24, such that the aperture 75 can be aligned with an aperture 25 in the levering member and secured with a pivot bolt 50, whereby the position locking member 70 can pivot in the longitudinal direction relative to the levering member 20. A slot 73 is provided in the threaded end 72 facing to the distal direction, which is sized to receive the angled end 32 of the distal outrigger member 30, as shown in FIGS. 1 and 10. An internally threaded lock nut 74 is disposed on the threaded end 72, such that the locking nut 74 can be rotated to abut against the angled end 32 of the outrigger member 30, thereby preventing angular movement between the levering member 20, outrigger members 30 and stabilizer member 40 as a result of tension in the ventral direction.

Figure 11:
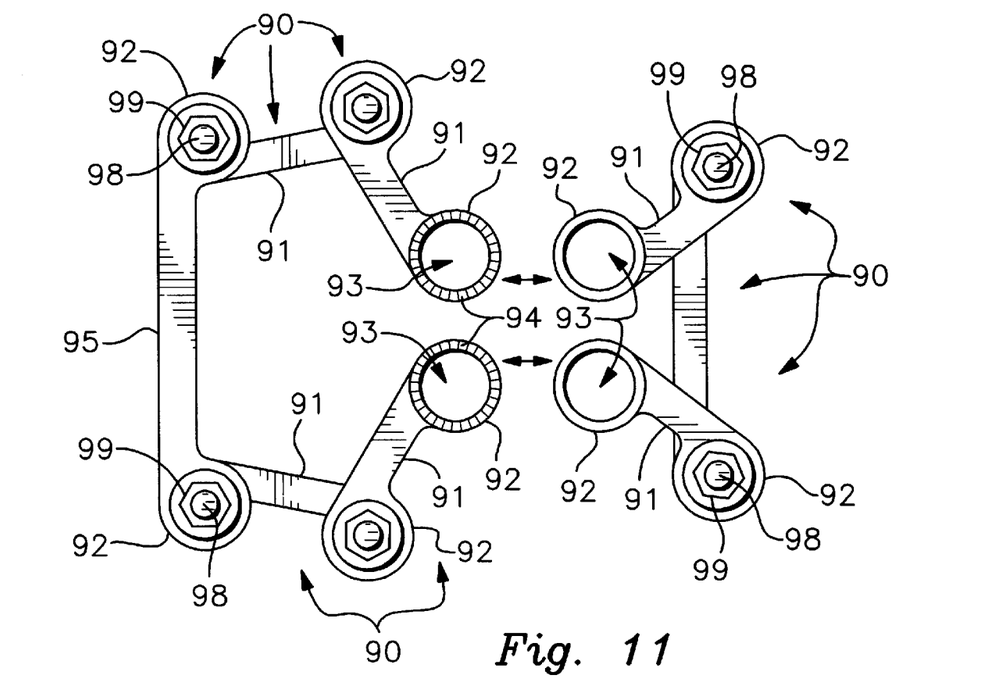
FIG. 11 is a view of the spinal linking members.
Figure 12:
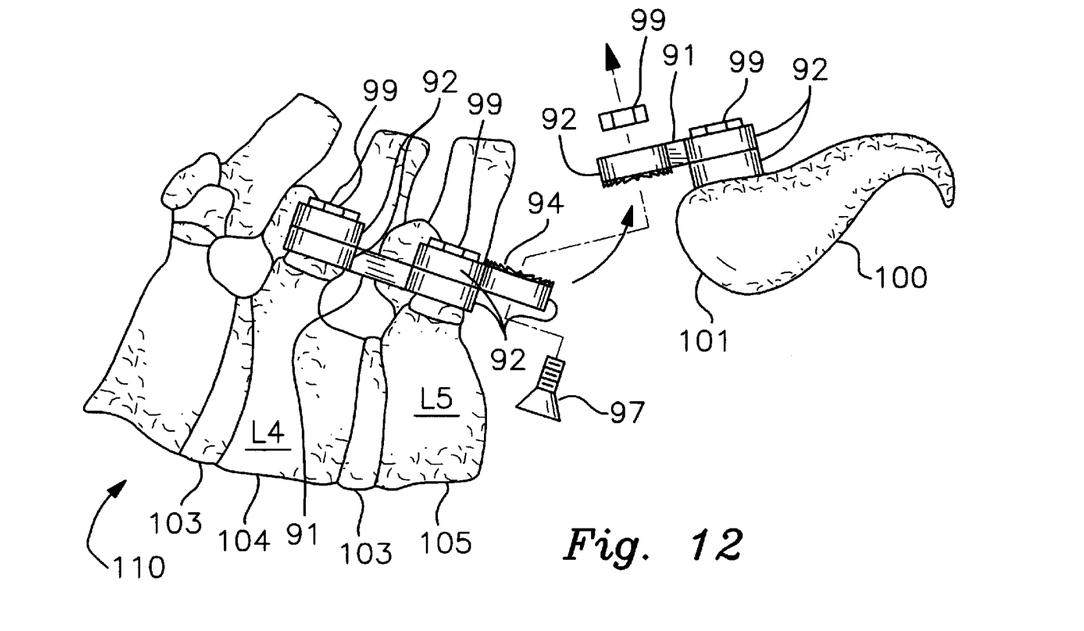
FIG. 12 is a lateral view of the spinal linking members as affixed to the sacrum and the vertebrae, prior to reduction.

The jack 10 is preferably utilized in conjunction with spine link members 90, which are shown in FIGS. 11 and 12, the structure, function and method of affixation of these link members 90 being more fully disclosed and described in U.S. Pat. No. 6,017,343, incorporated by reference herein. Alternatively, other spinal implant or structural linking members affixed to the sacrum 100 and vertebrae 110 may be used as substitutes for the spine link members 90 shown in the figures, such as rods or plates, provided means for temporary connection of the connector means 33 of the outrigger members 30 in a manner whereby movement of the outriggers 30 is transferred to the linking members is provided. The link members 90 comprise a central portion 91 joining two ends 92, the ends having relatively large circular apertures 93 to receive pedicle bolts 98 and lock nuts 99. At least one surface of the ends 92 is preferably provided with a mechanical interlocking or friction surface 94, which may comprise a series of radially extending ridges, such that relative rotation between the end 92 of one link member 90 and the aligned and abutting end 92 of a second link member 90 is hindered or precluded. The length of the central portion 91 will vary in order to achieve proper alignment of the apertures 93 of interconnected link members 90, with the longest central portion 91 defining a transverse bridging member 95 for a link member 90 which is mounted to extend transversely on either the base 101 of the sacrum 100 or one of the lumbar vertebrae 110. To affix a link member 90 to either the sacrum 100 or a vertebra 110, or to affix a link member 90 between two adjacent vertebrae 110 spanning the intervertebral disks 104, pedicle bolts 98 are securely implanted in the bone using known methodology, and the link members 90 are placed onto the pedicle bolts 98 and secured using lock nuts 74.

For the preferred methodology of the invention, a pair of link members 90 are positioned to extend generally longitudinally to connect the L4 vertebra 104 and the L5 vertebra 105. A transversely disposed link member 90 is positioned with its transverse bridging member 95 extending across the L4 vertebra 104 and with its ends 92 aligned with the distal ends 92 of the longitudinally disposed link members 90, and the three link members 90 are secured with a pair of lock nuts 99. Another pair of link members 90 is interconnected and locked to the proximal ends 92 of the longitudinally disposed link members 90 spanning the vertebrae 110, with the proximal ends 92 of these link members 90 extending away from the L5 vertebra 105 toward the sacrum 100. Correspondingly, a transversely disposed link member 90 is placed across the base 101 of the sacrum 100, and the proximal ends 92 of a pair of longitudinally disposed link members 90 are secured to the ends 92 of the transversely extending link member 90. The distal ends 92 of the longitudinally extending link members 90 extend away from the sacrum 100 toward the L5 vertebra 105. In this manner, the non-connected ends 92 of the link members 90 mounted onto the L5 vertebra 105 and the sacrum 100 can be joined to each other with an independent joining bolt member 97 and lock nut 99 after the spondylolisthesis reduction has been performed, creating a rigid structure comprising eight link members 90 joining and immobilizing the L4 vertebra 104, the L5 vertebra 105 and the sacrum 100.

Once the spine link members 90 are properly positioned and affixed in secure manner, the outrigger members 30 are affixed to the transverse bridging members 95 of the transversely disposed link members 90, with the connector means 33 centrally disposed along the transverse bridging members 95. Distraction, flexion or extension of the sacrum 100 can be accomplished by securing either the stabilizer member 40 or the levering member 20 to the outrigger members 30 and pivoting the proximal outrigger member 30 using the stabilizer member 40 or levering member 20 to provide a fulcrum point. The location of the intersection points between the stabilizer member 40 or levering member 20 and the outrigger members 30 affects the angular and linear relationships between the components, and is determined by patient physical factors and the manipulations necessary to be performed by the surgeon. Where the stabilizer member 40 is first utilized, the levering member 20 is then secured to the outrigger members 30 after the first stage of manipulations has been accomplished, with the chosen intersection points for the necessary angular and linear relationships again being determined by patient factors. Translation is accomplished by pulling the levering member handle 21, utilizing the sacrum 100 as a fulcrum such that the vertebrae 110 are moved in the dorsal direction. As manipulation progresses, it may be necessary to disconnect and reconnect the levering member 20 or the stabilizer member 40, or both, from the outrigger members 30 in order to adjust the angular and linear relationships between the components to provide for the proper manipulation. To overcome ligamentum taxis, to allow for adjustment of the position of the spine link members 90, or to secure the jack 10 in the final orientation for connection of the sacrum link members 90 to the L5 vertebra link members 90, the position locking member 70 is utilized. When the reduction has been accomplished such that the positional relationship between the vertebrae 110 and the sacrum 100 is as desired, the non-connected ends 92 of the link members 90 mounted onto the L5 vertebra 105 and the sacrum 100 will be properly aligned and are now joined to each other with an independent joining bolt member 97 and lock nut 99. With the vertebrae 110 and sacrum 100 now rigidly fixed by the link member 90 construct, the connector means 33 are loosened and the jack 10 is removed from the spine link members 90.

It is understood that equivalents and substitutions to certain elements set forth above may be obvious to those skilled in the art, and therefore the true scope and definition of the invention to be as set forth in the following claims.

I claim:

1. A method for manipulating the vertebrae and sacrum in the treatment of spondylolisthesis comprising the steps of:

providing link members adapted to be permanently affixed to the sacrum and the vertebrae;

affixing at least one link member to the sacrum;

affixing at least one link member to at least one vertebrae, where said at least one link member affixed to the sacrum is adapted to be rigidly joined to said at least one link member affixed to the vertebrae;

providing a jack device adapted to be temporarily connected to said link members whereby manipulation of said jack device is transferred through said link members to reposition said sacrum relative to said vertebrae, said jack device having a pair of outrigger members pivotally joined to a levering member, where the step of temporarily connecting said jack device to said link members is accomplished by connecting said outrigger members to said link members, and where the step of manipulating said jack device is accomplished by moving said levering member relative to said outrigger members, and further where said levering member is adapted to be joined to said outrigger members at various locations to vary the angular and linear relationship between said levering member and said outrigger members, and where the step of temporarily connecting said jack device to said link members is accomplished by first connecting said outrigger members to said link members and then connecting said levering member to said outrigger members in the desired angular and linear relationship;

temporarily connecting said jack device to said link members;

manipulating said jack device to reposition said sacrum and said at least one vertebrae such that said at least one link member affixed to said sacrum is aligned with said at least one link member affixed to said vertebrae in a manner which allows said link members to be joined;

joining said link members in a rigid and fixed manner; and removing said jack device from said link members.

2. The method of claim 1, where the step of affixing at least one link member to the sacrum comprises:

affixing three link members to the sacrum, where one said link member is mounted transversely onto the sacrum and two said link members are joined to said transversely mounted link member and affixed to the sacrum and extend longitudinally, such that each said longitudinally mounted link member has a free end;

and where the step of affixing at least one link member to at least one vertebrae comprises:

affixing five link members to the vertebrae, where one said link member is mounted transversely onto a first vertebrae, a first pair of said link members are joined to said transversely mounted link member and affixed to the first vertebrae and a second vertebrae, and a second pair of said link members are joined to said first pair of link members and affixed to the second vertebrae, such that each of said second pair of link members has a free end adapted to be joined to one of said free ends of said longitudinally mounted link members affixed to the sacrum.

3. The method of claim 2, where the step of temporarily connecting said jack to said link members is accomplished by connecting said jack device to said transversely mounted link members.

4. The method of claim 1, where said link members have apertures to receive bolt members, and where said link members are affixed to the sacrum and the vertebrae by providing pedicle bolts which are affixed into the sacrum and vertebrae, providing nuts which mate with said pedicle bolts, placing said apertures over said pedicle bolts, and connecting said nuts to said pedicle bolts;

and further where said link members are joined in a rigid and fixed manner to each other by providing joining bolts and nuts, aligning said apertures of said link members, inserting said joining bolts through said aligned apertures, and connecting said nuts to said joining bolts.

5. The method of claim 1, where the step of providing said jack device further comprises providing a jack device adapted to distract, flex, extend and translate the sacrum relative to the vertebrae, such that the step of repositioning the sacrum includes one or more movements chosen from the group of movements consisting of distraction, flexion, extension and translation.

6. The method of claim 1, where the step of providing said jack device further comprises providing a jack device having a locking member to secure the jack device in a fixed disposition, and further comprising the step of securing said jack member in a fixed disposition after alignment of said link members for joining.

7. A jack device for manipulating the vertebrae and sacrum in the treatment of spondylolisthesis and adapted for temporary connection to link members affixed to the sacrum and to the vertebrae, said jack device comprising:

a pair of elongated outrigger members each having connector means for temporarily connecting said outrigger members to link members affixed to the sacrum and to at least one vertebra, wherein a first outrigger member is adapted to be temporarily connected to a link member affixed to the sacrum and a second outrigger member is adapted to be temporarily connected to a link member affixed to at least one vertebrae;

a levering member pivotally connected to said pair of outrigger members such that movement of said levering member is transferred to one of said pair of outrigger members;

wherein said outrigger members and said levering member each further comprise a plural number of longitudinally spaced apertures adapted to receive pivot bolts, wherein said levering member is pivotally connected to said outrigger members by aligning pairs of said apertures and inserting said pivot bolts.

8. The device of claim 7, further comprising a stabilizer member pivotally connected to said pair of outrigger members.

9. The device of claim 8, further comprising a locking member, said locking member adapted to secure said outrigger members, said levering member and said stabilizer member in a fixed relationship.

10. The device of claim 8, wherein the combination of said outrigger members, said levering member and said stabilizing member define a polygonal configuration.

11. The device of claim 8, wherein said outrigger members, said levering member and said stabilizer member each further comprise a plural number of longitudinally spaced apertures adapted to receive pivot bolts, wherein said levering member and said stabilizer member are pivotally connected to said outrigger members by aligning pairs of said apertures and inserting said pivot bolts.

12. The device of claim 7, further comprising a locking member, said locking member adapted to secure said outrigger members and said levering member in a fixed relationship.

13. The device of claim 7, wherein said levering member further comprises two handles.

14. The device of claim 7, wherein said levering member further comprises a handle.

15. A method for manipulating adjacent vertebrae in the treatment of spondylolisthesis comprising the steps of:

providing link members adapted to be permanently affixed to the vertebrae, said vertebrae comprising an upper vertebra and a lower vertebra;

affixing at least one link member to said lower vertebra;

affixing at least one link member to said upper vertebra, where said at least one link member affixed to the lower vertebra is adapted to be rigidly joined to said at least one link member affixed to the upper vertebra;

providing a jack device adapted, to be temporarily connected to said link members whereby manipulation of said jack device is transferred through said link members to reposition said lower vertebra relative to said upper vertebra, said jack device having a pair of outrigger members pivotally joined to a levering member, where said levering member is adapted to be joined to said outrigger members at various locations to vary the angular and linear relationship between said levering member and said outrigger members;

temporarily connecting said jack device to said link members by first connecting said outrigger members to said link members and then connecting said levering member to said outrigger members in the desired angular and linear relationship;

manipulating said jack device by moving said levering member relative to said outrigger members to reposition said lower and upper vertebrae such that said at least one link member affixed to said lower vertebra is aligned with said at least one link member affixed to said upper vertebrae in a manner which allows said link members to be joined;

joining said link members in a rigid and fixed manner; and removing said jack device from said link members.

16. The method of claim 15, where the step of affixing at least one link member to the sacrum comprises:

affixing three link members to the sacrum, where one said link member is mounted transversely onto the sacrum and two said link members are joined to said transversely mounted link member and affixed to the sacrum and extend longitudinally, such that each said longitudinally mounted link member has a free end;

and where the step of affixing at least one link member to at least one vertebrae comprises:

affixing five link members to the vertebrae, where one said link member is mounted transversely onto a first vertebrae, a first pair of said link members are joined to said transversely mounted link member and affixed to the first vertebrae and a second vertebrae, and a second pair of said link members are joined to said first pair of link members and affixed to the second vertebrae, such that each of said second pair of link members has a free end adapted to be joined to said free ends of each of said first pair of link members affixed to the sacrum.

17. The method of claim 15, where said link members have apertures to receive bolt members, and where said link members are affixed to the sacrum and the vertebrae by providing pedicle bolts which are affixed into the sacrum and vertebrae, providing nuts which mate with said pedicle bolts, placing said apertures over said pedicle bolts, and connecting said nuts to said pedicle bolts;

and further where said link members are joined in a rigid and fixed manner to each other by providing joining bolts and nuts, aligning said apertures of said link members, inserting said joining bolts through said aligned apertures, and connecting said nuts to said joining bolts.

18. A jack device adapted for temporary connection to a first and a second link member affixed to the spine for the treatment of spondylolisthesis by manipulation of said first and second link members, said jack device comprising:

a pair of elongated outrigger members each having connector means for temporarily connecting said outrigger members to link members affixed to the spine, wherein a first outrigger member is adapted to be temporarily connected to a first link member and a second outrigger member is adapted to be temporarily connected to a second link member;

an elongated levering member pivotally connected to said first and said second outrigger members such that movement of said levering member is transferred to one of said outrigger members, wherein said levering member is connectable to said first outrigger member at multiple locations on both said levering member and said first outrigger member, and wherein said levering member is connectable to said second outrigger member at multiple locations on both said levering member and said second outrigger member.

19. The device of claim 18, further comprising an elongated stabilizer member pivotally connected to said first and said second outrigger members, wherein said stabilizer member is connectable to said first outrigger member at multiple locations on both said stabilizer member and said first outrigger member, and wherein said stabilizer member is connectable to said second outrigger member at multiple locations on both said stabilizer member and said second outrigger member.

20. The device of claim 19, further comprising a locking member, said locking member adapted to secure said outrigger members, said stabilizer member and said levering member in a fixed relationship.

21. The device of claim 18, further comprising a locking member, said locking member adapted to secure said outrigger members and said levering member in a fixed relationship.

22. The device of claim 21, wherein the combination of said outrigger members, said stabilizer member and said levering member defines a polygonal configuration.

23. A method for manipulating the vertebrae and sacrum in the treatment of spondylolisthesis comprising the steps of:

providing link members adapted to be permanently affixed to the sacrum and the vertebrae;

affixing three link members to the sacrum, where one said link member is mounted transversely onto the sacrum and two said link members are joined to said transversely mounted link member and affixed to the sacrum and extend longitudinally, such that each said longitudinally mounted link member has a free end;

affixing five link members to the vertebrae, where one said link member is mounted transversely onto a first vertebrae, a first pair of said link members are joined to said transversely mounted link member and affixed to the first vertebrae and a second vertebrae, and a second pair of said link members are joined to said first pair of link members and affixed to the second vertebrae, such that each of said second pair of link members has a free end adapted to be joined to one of said free ends of said longitudinally link members affixed to the sacrum;

providing a jack device adapted to be temporarily connected to said link members whereby manipulation of said jack device is transferred through said link members to reposition said sacrum relative to said vertebrae;

temporarily connecting said jack device to said link members;

manipulating said jack device to reposition said sacrum and said at least one vertebrae such that said at least one link member affixed to said sacrum is aligned with said at least one link member affixed to said vertebrae in a manner which allows said link members to be joined;

joining said link members in a rigid and fixed manner; and removing said jack device from said link members.

24. The method of claim 23, where the step of providing said jack device further comprises providing a jack device having a locking member to secure the jack device in a fixed disposition, and further comprising the step of securing said jack member in a fixed disposition after alignment of said link members for joining.

25. The method of claim 23, where said step of providing said jack device further comprises providing a jack device having a pair of outrigger members pivotally joined to a levering member, where the step of temporarily connecting said jack device to said link members is accomplished by connecting said outrigger members to said link members, and where the step of manipulating said jack device is accomplished by moving said levering member relative to said outrigger members.

26. The method of claim 25, where said levering member is adapted to be joined to said outrigger members at various locations to vary the angular and linear relationship between said levering member and said outrigger members, and where the step of temporarily connecting said jack device to said link members is accomplished by first connecting said outrigger members to said link members and then connecting said levering member to said outrigger members in the desired angular and linear relationship.

27. The method of claim 23, where the step of temporarily connecting said jack to said link members is accomplished by connecting said jack device to said transversely mounted link members.

28. The method of claim 23, where said link members have apertures to receive bolt members, and where said link members are affixed to the sacrum and the vertebrae by providing pedicle bolts which are affixed into the sacrum and vertebrae, providing nuts which mate with said pedicle bolts, placing said apertures over said pedicle bolts, and connecting said nuts to said pedicle bolts;

and further where said link members are joined in a rigid and fixed manner to each other by providing joining bolts and nuts, aligning said apertures of said link members, inserting said joining bolts through said aligned apertures, and connecting said nuts to said joining bolts.

29. The method of claim 23, where the step of providing said jack device further comprises providing a jack device adapted to distract, flex, extend and translate the sacrum relative to the vertebrae, such that the step of repositioning the sacrum includes one or more movements chosen from the group of movements consisting of distraction, flexion, extension and translation.

30. A method for manipulating the vertebrae and sacrum in the treatment of spondylolisthesis comprising the steps of:

providing link members adapted to be permanently affixed to the sacrum and the vertebrae, where said link members have apertures to receive bolt members, and where said link members are affixed to the sacrum and the vertebrae by providing pedicle bolts which are affixed into the sacrum and vertebrae, providing nuts which mate with said pedicle bolts, placing said apertures over said pedicle bolts, and connecting said! nuts to said pedicle bolts, and further where said link members are joined in a rigid and fixed manner to each other by providing joining bolts and nuts, aligning said apertures of said link members, inserting said joining bolts through said aligned apertures, and connecting said nuts to said joining bolts;

affixing at least one link member to the sacrum;

affixing at least one link member to at least one vertebrae, where said at least one link member affixed to the sacrum is adapted to be rigidly joined to said at least one link member affixed to the vertebrae;

providing a jack device adapted to be temporarily connected to said link members whereby manipulation of said jack device is transferred through said link members to reposition said sacrum relative to said vertebrae;

temporarily connecting said jack device to said link members;

manipulating said jack device to reposition said sacrum and said at least one vertebrae such that said at least one link member affixed to said sacrum is aligned with said at least one link member affixed to said vertebrae in a manner which allows said link members to be joined;

joining said link members in a rigid and fixed manner; and removing said jack device from said link members.

31. The method of claim 30, where the step of providing said jack device further comprises providing a jack device having a locking member to secure the jack device in a fixed disposition, and further comprising the step of securing said jack member in a fixed disposition after alignment of said link members for joining.

32. The method of claim 30, where said step of providing said jack device further comprises providing a jack device having a pair of outrigger members pivotally joined to a levering member, where the step of temporarily connecting said jack device to said link members is accomplished by connecting said outrigger members to said link members, and where the step of manipulating said jack device is accomplished by moving said levering member relative to said outrigger members.

33. The method of claim 32, where said levering member is adapted to be joined to said outrigger members at various locations to vary the angular and linear relationship between said levering member and said outrigger members, and where the step of temporarily connecting said jack device to said link members is accomplished by first connecting said outrigger members to said link members and then connecting said levering member to said outrigger members in the desired angular and linear relationship.

34. The method of claim 30, where the step of affixing at least one link member to the sacrum comprises:

affixing three link members to the sacrum, where one said link member is mounted transversely onto the sacrum and two said link members are joined to said transversely mounted link member and affixed to the sacrum and extend longitudinally, such that each said longitudinally mounted link member has a free end;

and where the step of affixing at least one link member to at least one vertebrae comprises:

affixing five link members to the vertebrae, where one said link member is mounted transversely onto a first vertebrae, a first pair of said link members are joined to said transversely mounted link member and affixed to the first vertebrae and a second vertebrae, and a second pair of said link members are joined to said first pair of link members and affixed to the second vertebrae, such that each of said second pair of link members has a free end adapted to be joined to said free ends of each of said first pair of link members affixed to the sacrum.

35. The method of claim 34, where the step of temporarily connecting said jack to said link members is accomplished by connecting said jack device to said transversely mounted link members.

36. The method of claim 30, where the step of providing said jack device further comprises providing a jack device adapted to distract, flex, extend, and translate the sacrum relative to the vertebrae, such that the step of repositioning the sacrum includes one or more movements chosen from the group of movements consisting of distraction, flexion, extension and translation.

37. A jack device for manipulating the vertebrae and sacrum in the treatment of spondylolisthesis and adapted for temporary connection to link members affixed to the sacrum and to the vertebrae, said jack device comprising:

a pair of elongated outrigger members each having connector means for temporarily connecting said outrigger members to link members affixed to the sacrum and to at least one vertebra, wherein a first outrigger member is adapted to be temporarily connected to a link member affixed to the sacrum and a second outrigger member is adapted to be temporarily connected to a link member affixed to at least one vertebrae;

a levering member pivotally connected to said pair of outrigger members such that movement of said levering member is transferred to one of said pair of outrigger members;

a stabilizer member pivotally connected to said pair of outrigger members;

wherein said outrigger members, said levering member and said stabilizer member each further comprise a plural number of longitudinally spaced apertures adapted to receive pivot bolts, wherein said levering member and said stabilizer; member are pivotally connected to said outrigger members by aligning pairs of said apertures and inserting said pivot bolts.

38. The device of claim 37, further comprising a locking member, said locking member adapted to secure said outrigger members, said levering member and said stabilizer member in a fixed relationship.

39. The device of claim 38, wherein said levering member further comprises two handles.

40. The device of claim 37, wherein the combination of said outrigger members, said levering member and said stabilizing member define a polygonal configuration.

41. The device of claim 37, wherein said levering member further comprises a handle.

\* \* \* \* \*